US00PP09388P

United States Patent [19]

Schumann et al.

[11] Patent Number: Plant 9,388

[45] Date of Patent: Nov. 28, 1995

[54] GERANIUM PLANT NAMED 'FISPLOSIVE'

[75] Inventors: Ingeborg Schumann, Albstadt; Angelika Utecht, Montabaur, both of Germany

[73] Assignee: Florfis AG, Binningen, Switzerland

[21] Appl. No.: 360,343

[22] Filed: Dec. 21, 1994

[51] Int. Cl.[6] ..... A01H 5/00

[52] U.S. Cl. ..... Plt./87.12

[58] Field of Search ..... Plt./87.12

*Primary Examiner*—James R. Feyrer
*Attorney, Agent, or Firm*—Foley & Lardner

[57] ABSTRACT

A new and distinct cultivar of geranium named Fisplosive, particularly characterized by the combined features of pink flower color with a slight violet tint, semi-double flower type, deep green foliage without zonation, compact growth habit, early spring flower response, and rich flowering throughout the year.

1 Drawing Sheet

The present invention comprises a new and distinct cultivar of geranium, botanically known as *Pelargonium, zonale* l'Hert, and hereinafter referred to by the cultivar name Fisplosive.

Fisplosive is a product of a planned breeding program which had the objective of creating new geranium cultivars with pink flower color, dark green foliage, and single or almost single flower form.

Fisplosive was originated from a hybridization made by inventor Ingeborg Schumann in a controlled breeding program in Galdar, Gran Canaria, Spain in 1989. The female parent was the patented cultivar Fiswig, disclosed in U.S. Plant Pat. No. 7,385, and having single red flowers and dark green leaves without or with very weak zonation. The male parent of Fisplosive was the commercial cultivar Kristall, characterized by its light violet semi-double flowers and medium to light green foliage without zonation.

Fisplosive was discovered and selected as one flowering plant within the progeny of the stated cross by Angelika Utecht in 1990 in a controlled environment in Galdar, Gran Canaria, Spain.

The first act of asexual reproduction of Fisplosive was accomplished when vegetative cuttings were taken from the initial selection in autumn 1990 in a controlled environment in Galdar, Gran Canaria, Spain, by, or under the supervision of, Angelika Utecht.

Horticultural examination of plants grown from these cuttings initiated in May 1991, and continuing thereafter, has demonstrated that the combination of characteristics as herein disclosed for Fisplosive are firmly fixed and are retained through successive generations of asexual reproduction.

Fisplosive has not been observed under all possible environmental conditions. The phenotype may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characeristics of Fisplosive, which, in combination, distinguish this geranium as a new and distinct cultivar:

1. Pink flower color with a slight violet tint.
2. Large, weakly semi-double flowers.
3. Deep green foliage without zonation.
4. Compact growth habit.
5. Early flower response.

6. Rich flowering throughout the year.

Of the many commercial cultivars known to the present inventor, none can be closely compared to Fisplosive. Compared to the male parent Kristall, Fisplosive has a more pink flower color and more intense green foliage.

The accompanying color photographic drawing shows typical flower and foliage charcteristics of Fisplosive, with colors being as true as possible with illustrations of this type.

In the following description, color references are made to The Royal Horticultural Society Colour Chart. The color values were determined indoors in May from plants grown indoors in Hillscheid, Federal Republic of Germany.

Classification:

*Botanical.*—A hybrid of the species *Pelargonium zonale* l'Hert.

*Commercial.*—Zonal geranium, cv., Fisplosive.

Inflorescence

Umbel:

*Shape.*—Umbrella-shaped.
*Average diameter.*—110 mm.
*Averge depth.*—45 mm.
*Peduncle length.*—185 mm.
*Peduncle color.*—Green, with anthocyanin in the middle part.
*Pedicel length.*—31 mm.
*Pedicel color.*—Light to dark red.
*Number of flowers per umbel.*—25–30.

Corolla:

*Average diameter.*—50 mm.
*Form.*—Semi-double.
*Number of petals.*—8–9.
*Number of petaloids.*—1.
*Color (general tonality from a distance of three meters).*—Pink with variable violet tint.
*Color of upper and lower petals.*—Between 58B-C and 68A-B.
*Markings on upper petals.*—Weak salmon coloring at the base.
*Color of lower surface of petals.*—68B-C and white, marbled.
*Color of sepals.*—Green, dark red base.
*Number of sepals.*—5.

Bud:

*Shape.*—Elliptical.
*Color (adaxial).*—Medium green.
*Color (abaxial).*—Pink, marbled.

Reproductive organs:

*Androecium.*—5–7 fertile anthers, white and pink filaments and orange pollen.

*Gynoecium.*—5–6 lobed stigma, purple-pink style and pink stigma.

Spring flowering response periods: In Hillscheid, Federal Republic of Germany, in 1993 plants had on average 1.7 flowers opened 11 weeks after planting of unrooted cuttings.

Outdoor flower production: The flower count in 1992 in Hillscheid, Federal Republic of Germany was between 55 and 60 flowers per plant for May through August observation period.

Durability: Good shatter resistance and good rain resistance due to the weakly semi-double flower form.

Plant

Foliage:

*Form.*—Kidney-shaped.

*Margin.*—Bicrenated.

*Size of leaf.*—90 mm.

*Color of upper surface.*—Uniform deep green, approximately 137B.

*Color (zonation).*—No zonation.

*Tolerance of botrytis.*—Average.

General appearance and form:

*Internode length.*—10–15 mm.

*Branching pattern.*—1.5 branches per week.

*Height.*—28 cm (in September, based on 32-week-old plants).

It is claimed:

1. A new and distinct cultivar of geranium plant named Fisplosive, as illustrated and described.

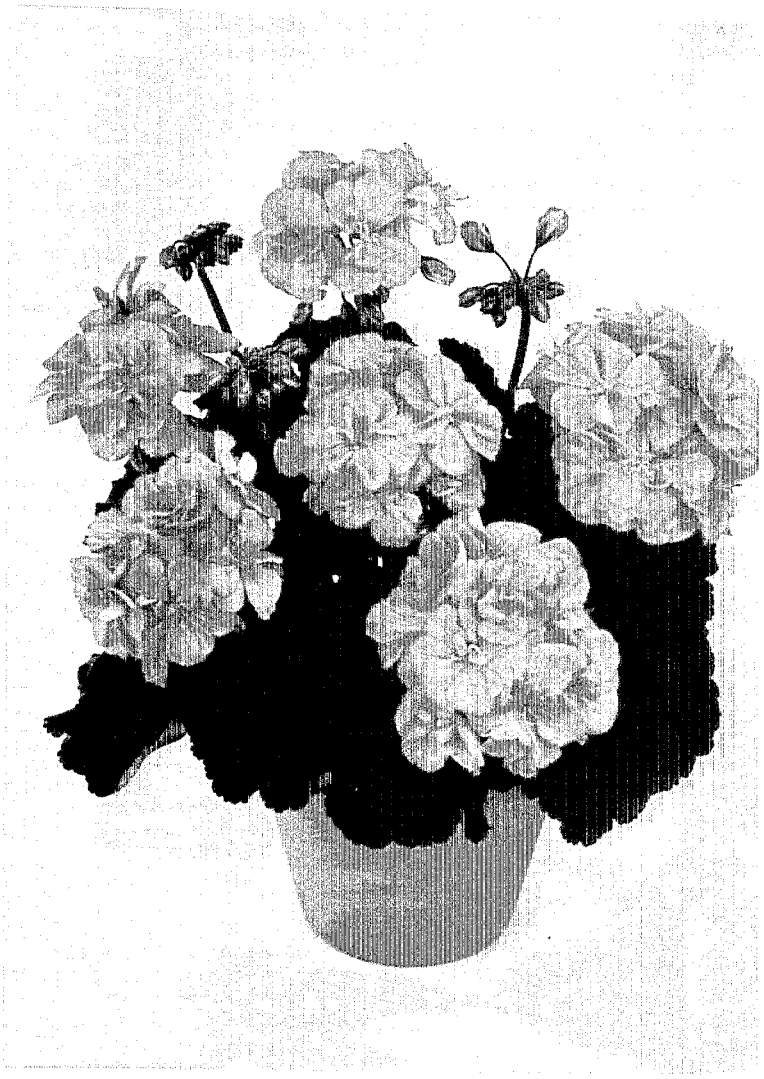

* * * * *